United States Patent [19]

Ernst et al.

[11] Patent Number: 4,550,182

[45] Date of Patent: Oct. 29, 1985

[54] PREPARATION OF α-TOCOPHEROL

[75] Inventors: Hansgeorg Ernst, Ludwigshafen; Henning-Peter Gehrken, Lambsheim; Joachim Paust, Neuhofen, all of Fed. Rep. of Germany

[73] Assignee: BASF Aktiengesellschaft, Ludwigshafen, Fed. Rep. of Germany

[21] Appl. No.: 588,374

[22] Filed: Mar. 12, 1984

[30] Foreign Application Priority Data

Mar. 15, 1983 [DE] Fed. Rep. of Germany ....... 3309158

[51] Int. Cl.$^4$ .................................................. C07D 311/72
[52] U.S. Cl. .................................................. 549/408
[58] Field of Search ........................................ 549/408

[56] References Cited

U.S. PATENT DOCUMENTS

| 3,139,442 | 6/1964 | Rudner et al. | 549/408 |
| 4,051,153 | 9/1977 | Cohen et al. | 549/408 |
| 4,086,249 | 4/1978 | Chan et al. | 549/408 |

*Primary Examiner*—Ethel G. Love
*Attorney, Agent, or Firm*—Oblon, Fisher, Spivak, McClelland & Maier

[57] ABSTRACT

A process for the preparation of α-tocopherol of the formula I by reacting a chroman derivative with a $C_{14}$-Grignard reagent using a di-alkali metal tetrahalocuprate catalyst in a Schlosser-Fouquet reaction, wherein a chroman derivative of the general formula II where Y is a leaving group, especially Br, is used and is reacted, at from $-70°$ to $0°$ C., first with a solution of about 1 equivalent of a Grignard compound of the general formula III $$X-Mg-R \qquad (III)$$

where X is Cl, Br or I and R is straight-chain or branched alkyl of 1 to 14 carbon atoms, preferably methyl, ethyl or and then with a solution of a Grignard reagent of the formula IIIa in an ether solvent and a solution of a di-alkali metal tetrahalocuprate in an ether solvent.

The novel process simplifies the preparation of 2RS,4'RS,8'RS-, 2R,4'RS,8'RS- or 2R,4'R,8'R-α-tocopherol by reacting a chroman structural unit, containing a $C_2$ side-chain in the 2-position, with the corresponding $C_{14}$-Grignard compound.

13 Claims, No Drawings

PREPARATION OF α-TOCOPHEROL

The present invention relates to an improved process for the preparation of α-tocopherol by reacting a chroman derivative with a $C_{14}$-Grignard reagent in the presence of a di-alkali metal tetrahalocuprate, preferably of di-lithium tetrachlorocuprate. This process not only permits the preparation of racemic α-tocopherol but also provides an advantageous method for preparing the product possessing the naturally occurring configuration, (2R,4'R,8'R)-α-tocopherol, as well as (2R,4'RS,8'RS)-α-tocopherol or any other α-tocopherol stereoisomers.

In recent years, vitamin E (α-tocopherol) has become important as an antioxidant and in both human and animal nutrition. A great variety of processes for the synthesis of all-rac-α-tocopherol has been disclosed. Siebrell and Harris give a survey of these in "Vitamins", V (1972), 165 et seq. In the more recent literature, processes for the preparation of natural optically active vitamin E (2R,4'R,8'R-α-tocopherol) have also been described (cf. N. Cohen et al., J. Am. Chem. Soc. 101 (1979), 6710–16). The preparation of stereoisomers of α-tocopherol is of interest because the different stereoisomers exhibit different intensity of biological action. Of the three centers of asymmetry of natural vitamin E, of the formula

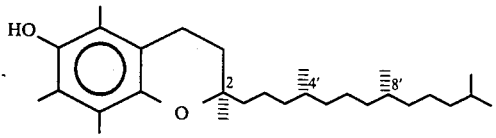

the center on the carbon atom in the 2-position is particularly important in respect of the biological action (cf. S. Ames, "Lipids" No. 6 (1971), 281–290, especially 285). For example, the activity of the (2R,4'RS,8'RS)-epimer is 5 times greater than that of the (2S,4'RS,8'RS)-epimer. Since the C-4' and C-8' centers have only a minor influence on the activity of the molecule even the synthesis of (2R,4'RS,8'RS)-α-tocopherol alone suffices to achieve improved biological activity.

Cohen et al., Helv. Chim. Acta 64 (1981), No. 4, 1158–73, describe the preparation of all 8 possible stereoisomers of -tocopheryl acetate in high chemical and stereoisomeric purity. For example, these authors obtained the (2R,4'RS,8'RS)-isomer by reacting racemic tetrahydronerolidol with triphenylphosphonium bromide in $CH_2Cl_2$ and carrying out a Wittig reaction of the resulting triphenylphosphonium salt with (+)-(S)-6-benzyloxy-2,5,7-tetramethylchroman-2-carbaldehyde in the presence of sodium methylate, followed by hydrogenation of the α-tocodiene obtained over Pd/C.

The preparation of racemic and optically active α-tocopherol by coupling a corresponding chroman derivative, which already contains a $C_2$ side-chain in the 2-position, with a suitable $C_{14}$ structural unit is described in German Laid-Open Application DOS No. 2,602,509. According to this publication, a chroman derivative of the formula

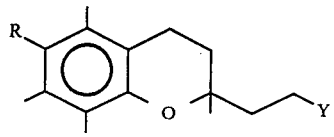

where R is an ether and Y is a leaving group is coupled, in an organic solvent, with a Grignard compound of the general formula IV

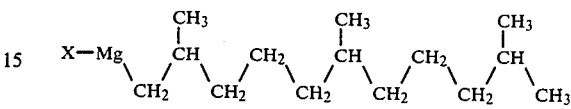

using a di-alkali metal tetrahalocuprate catalyst in a Schlosser-Fouquet reaction (cf. Angew. Chem. Int. Ed. 13 (1974), 82 et seq. and ibid. 13 (1974), 701 et seq.).

A disadvantage of this process is that after the coupling reaction for the preparation of α-tocopherol, the ether protective group initially introduced into the 6-position of the chroman system before the coupling reaction has to be removed again. These 2 additional reaction steps inevitably reduce the yield and entail additional starting material costs.

It is an object of the present invention to provide a more advantageous method of preparation of α-tocopherol by coupling a chroman derivative, containing a $C_2$ side-chain in the 2-position, with an appropriate $C_{14}$ structural unit.

We have found that this object is achieved by a process for the preparation of α-tocopherol of the formula I

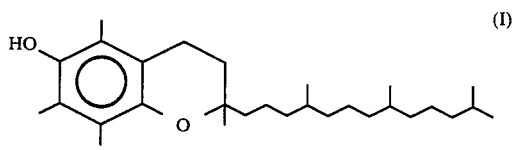

(I)

by reacting a chroman derivative with a $C_{14}$-Grignard reagent using a di-alkali metal tetrahalocuprate catalyst in a Schlosser-Fouquet reaction, wherein (a) a chroman derivative of the general formula II

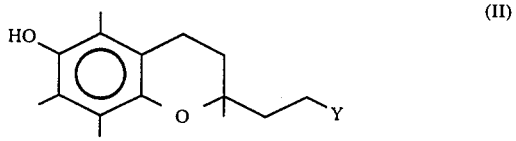

(II)

where Y is one of the leaving groups —Br, —I, -p-tosyl or benzenesulfonyl, especially —Br, is used and is reacted, at from —70° to 0° C., preferably from —25° to —15° C., (b) first with a solution of from 0.8 to 1.1, preferably from 0.85 to 1.0, equivalent of a Grignard reagent of the general formula III

(III)

where X is Cl, Br or I and R is straight-chain or branched alkyl of 1 to 14 carbon atoms, preferably methyl, ethyl or

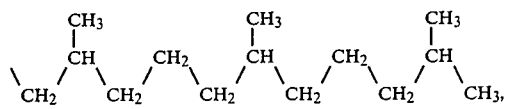

and then (c) with a solution of from 1.05 to 2.0 equivalents, preferably from 1.2 to 1.7 equivalents, of a Grignard reagent of the formula IIIa

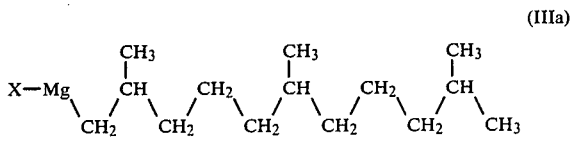

in an ether solvent and in the presence of copper ions, preferably in the presence of a solution of a di-alkali metal tetrahalocuprate, especially of di-lithium tetrachlorocuprate, in an ether solvent.

The novel process is of particular importance for the preparation of (2R,4′RS,8′RS)-α-tocoperol and of the naturally occurring (2R,4′R,8′R)-α-tochopherol.

To prepare these compounds, it is advantageous to react (2S)-2,5,7,8-tetramethyl-6-hydroxy-2-(2′-bromoethyl)-chroman, in step (c), with a (2RS,6RS)-2,6,10-trimethyl-1-undecyl-magnesium halide or a (2R,6R)-2,6,10-trimethyl-1-undecyl-magnesium halide respectively. The novel process shortens the method of synthesis of α-tocopherol of the formula I inasmuch as in the reaction according to the invention, of a chroman derivative with a $C_{14}$-Grignard reagent, no prior introduction, and accordingly no subsequent removal, of a protective group is necessary.

Suitable chroman derivatives of the general formula II are those where Y is a leaving group, which leaves during the Grignard reaction. Specific examples are leaving groups such as —Br, —I, -p-tosyl and -benzenesulfonyl, especially —Br.

The chroman derivatives may be employed in the form of the racemate or in an optically active form.

The coupling reaction is carried out in an inert ether solvent, for example in tetrahydrofuran (THF), dioxane, diethyl ether, dimethoxyethane or diethylene glycol dimethyl ether. THF is preferred.

The Grignard compounds of the general formula III or IIIa may be prepared in a manner known per se, for example by converting a corresponding alcohol to a halide and treating the latter with metallic magnesium in an ether solvent, advantageously in THF, at an elevated temperature, for example at from 40° to 80° C. An advantageous method for preparing (2R,6R)-1-chloro-2,6,10-trimethylundecane is described in German Patent . . . (German Patent Application No. P 31 39 238), which does not constitute a prior publication.

To carry out the coupling reaction, the chroman derivative II is dissolved in the ether solvent and to the solution, at from −70° to 0° C., preferably from −25° to −15° C., there is next added from 0.8 to 1.1 equivalents, preferably from 0.85 to 1.0 equivalent, of an approximately 1–2-molar solution of a Grignard reagent of the formula III. This reagent can be the Grignard compound IIIa subsequently employed for the coupling reaction or any other alkyl-Grignard compound. Even unsaturated compounds, such as vinyl-magnesium halides, may be used but these do not offer any advantages since on the one hand they are more difficult to prepare and on the other hand the yields obtained with them are lower.

Advantageously, methyl-magnesium bromide or ethyl-magnesium bromide is used.

The Grignard compounds used in this reaction step serve to deprotonize the phenolic OH group of the chroman compound in the manner of a Zerewitinoff reaction (cf. Organikum, VEB Deutscher Verlag der Wissenschaften, Berlin, 1972, 11th edition, page 551) and thus to convert it to a magnesium phenolate group.

For this purpose, the two components are reacted in the stated temperature range for from 15 minutes to 4 hours, preferably from 30 minutes to 2 hours.

Thereafter, the Grignard compound IIIa, in the form of an approximately 1–2-molar solution in an ether solvent, is added to the reaction mixture at the same temperature. For this step, IIIa is used in a small molar excess (1.05–2 equivalents, based on II, preferably 1.2–1.7 equivalents).

After addition of the di-alkali metal tetrahalocuprate, which is advantageously employed in the form of an about 0.5-molar solution in the ether solvent, the reaction mixture is stirred for about 2–3 hours at from −70° to 0° C., preferably from −25° to −15° C., is then allowed to come to room temperature and is stirred at room temperature for 4–20 hours. The preferred di-alkali metal tetrahalocuprate is di-lithium tetrachlorocuprate. In general, it is used in an amount of about 0.5–4 mole %, preferably 1–3 mole %, based on the Grignard compound IIIa employed.

The reaction mixture is worked up in a conventional manner, for example by adding a saturated ammonium chloride solution and extracting with diethyl ether.

The process according to the invention substantially simplifies the preparation of 2RS,4′RS,8′RS-, 2R,4′RS,8′RS- or 2R,4′R,8′R-α-tocopherol by reaction of a chroman structural unit, containing a $C_2$ side-chain in the 2-position, with the appropriate $C_{14}$-Grignard compound.

EXAMPLE 1

(a) Preparation of a (2RS,6RS)-2,6,10-trimethyl-1-undecylmagnesium chloride solution 10 ml of tetrahydrofuran (THF), followed by a solution of 13.95 g (60 millimoles) of (2RS,6RS)-1-chloro-2,6,10-trimethylundecane in 20 ml of THF, were added dropwise to 1.48 g (61.8 millimoles) of magnesium shavings which had been activated by surface etching with a crystal of iodine. The mixture was stirred for 2 hours at +70° C.

(b) Reaction with the Grignard reagents 15.65 g (50 millimoles) of (2RS)-2,5,7,8-tetramethyl-6-hydroxy-2-(2-bromoethyl)-chroman were dissolved in 30 ml of absolute THF, 33.5 ml of a 1.5-molar solution of methyl-magnesium bromide in THF were added dropwise to the above solution at −20° C. and the resulting reaction mixture was stirred for 30 minutes at −20° C. Thereafter there were added, first a solution, prepared as in (a) above, of (2RS,6RS)-2,6,10-trimethyl-1-undecyl-magnesium chloride and then 3.3 ml of an 0.5-molar solution of di-lithium tetrachlorocuprate, and the resulting reaction mixture was stirred for 3 hours at −20° C. and then for 15 hours at room temperature.

(c) Working up the reaction mixture

The reaction mixture obtained as in (b) above was mixed with 100 ml of a saturated ammonium chloride solution and extracted with diethyl ether. The combined organic phases were washed with saturated ammonium chloride solution and 5% strength sodium bicarbonate solution and dried over MgSO$_4$, and the solvent was evaporated off under reduced pressure, leaving on oily product. Distillation in a bulb tube at 240° C./0.3 mbar gave 14.8 g of α-tocopherol. This corresponds to a yield of 69% of theory.

EXAMPLE 2

(a) Preparation of a (2RS,6RS)-2,6,10-trimethyl-1-undecylmagnesium chloride solution 4.08 g (17 millimoles) of (2RS,6RS)-1-chloro-2,6,10-trimethyl-undecane in 5 ml of absolute THF were added dropwise to 0.43 g (17.8 millimoles) of magnesium shavings which had been activated by surface etching with a crystal of iodine. The mixture was stirred for 2 hours at +70° C.

(b) Reaction with the Grignard reagents 3.13 g (10 millimoles) of (2RS)-2,5,7,8-tetramethyl-6-hydroxy-2-(2-bromoethyl)-chroman were dissolved in 10 ml of absolute THF. A solution of ethyl-magnesium bromide which had been prepared by reacting 0.25 g (10.3 millimoles) of magnesium in 3 ml of THF with a solution of 1.1 g (10.0 millimoles) of bromoethane in 5 ml of THF and stirring for 1 hour at +40° C. was added dropwise to the above solution at −20° C. The resulting reaction mixture was stirred for 1 hour at −20° C. and then there were added to it the (2RS,6RS)-2,6,10-trimethyl-1-undecyl-magnesium chloride solution prepared in Example 2a, followed by 0.7 ml of an 0.5-molar solution of di-lithium tetrachlorocuprate in absolute THF. The batch was then stirred for 3 hours at −20° C. and 16 hours at room temperature. The reaction mixture was worked up as described in Example 1c and 3.7 g of α-tocopherol were isolated by bulb tube distillation at 220° C./0.2 mbar. This corresponds to a yield of 86% of theory.

EXAMPLE 3

7.38 g (25 millimoles) of (2RS)-2,5,7,8-tetramethyl-6-hydroxy-2-(2-bromoethyl)-chroman were dissolved in 15 ml of absolute THF. 15.8 ml of a 1.5-molar solution of methyl-magnesium bromide in THF (23.75 millimoles) were added dropwise to the above solution at −20° C. and the batch was stirred for 1 hour at −20° C.

A solution of (2RS,6RS)-2,6,10-trimethyl-1-undecyl-magnesium chloride, prepared by the method of Example 1a from 0.67 g (28 millimoles) of magnesium shavings and 6.40 g (27.5 millimoles) of (2RS,6RS)-1-chloro-2,6,10-trimethyl-undecane in 16 ml of THF, was added to the reaction mixture obtained above, at −20° C.

1.7 ml of an 0.5-molar solution of di-lithium tetrachlorocuprate in THF were then added to the reaction mixture at −20° C. and the batch was stirred for 3 hours at −20° C. and 16 hours at room temperature.

After the mixture had been worked up by the method of Example 1c, purification by distillation in a bulb tube at 230° C./0.2 mbar gave 6.9 g of α-tocopherol. This corresponds to a yield of 64% of theory.

EXAMPLE 4

7.38 g (25 millimoles) of (2RS)-2,5,7,8-tetramethyl-6-hydroxy-2-(2-bromoethyl)-chroman were dissolved in 20 ml of THF. A solution of (2RS,6RS)-2,6,10-trimethyl-1-undecyl-magnesium chloride, prepared by the method of Example 1a from 1.82 g (76 millimoles) of magnesium and 17.44 g (75 millimoles) of (2RS,6RS)-1-chloro-2,6,10-trimethylundecane in 38 ml of THF was added to the above solution at −20° C.

1.8 ml of an 0.5-molar solution of di-lithium tetrachlorocuprate in THF were then added dropwise at −20° C. The reaction mixture was stirred for 3 hours at −20° C. and 15 hours at room temperature.

The mixture was worked up by the method of Example 1c. Distillation to a bulb tube at 240° C./0.3 mbar gave 8.7 g of α-tocopherol. This corresponds to a yield of 81% of theory.

EXAMPLE 5

7.38 g (25 millimoles) of (2S)-2,5,7,8-tetramethyl-6-hydroxy-2-(2-bromoethyl)-chroman were dissolved in 15 ml of absolute THF. 15.8 ml of a 1.5-molar solution of methyl-magnesium bromide (23.75 millimoles) in THF were added dropwise to the above solution at −70° C. The mixture was stirred for 1½ hours at −70° C. and a solution of (2RS,6RS)-2,6,10-trimethyl-1-undecyl-magnesium chloride, prepared by the method of Example 1a from 0.92 g (38.5 millimoles) of magnesium and 8.72 g of (2RS,6RS)-1-chloro-2,6,10-trimethylundecane in 20 ml of THF, followed by 1.7 ml of an 0.5-molar solution of di-lithium tetrachlorocuprate in THF, were added to the above mixture at −70° C. The reaction mixture was then stirred for 1½ hours at −70° C., 2 hours at −30° C. and 15 hours at room temperature.

After the mixture had been worked up by the method of Example 1c, bulb tube distillation at 220° C. 0.2 mbar gave 7.53 g of (2R,4'RS,8'RS)-α-tocopherol. This corresponds to a yield of 70% of theory.

The (2R,4'RS,8'RS)-α-tocopherol was converted to the acetate in a conventional manner. $[\alpha]_0^{25} = +2.54°$ (C=5.2/ethanol)

EXAMPLE 6

7.38 g (25 millimoles) of (2S)-2,5,7,8-tetramethyl-6-hydroxy-2-(2-bromoethyl)-chroman were dissolved in 15 ml of absolute THF. 15.8 ml of a 1.5-molar solution of methyl-magnesium bromide (23.75 millimoles) in THF were added dropwise to the above solution at −20° C. and the mixture was then stirred for 1 hour at the same temperature. Thereafter, a solution of (2R,6R)-2,6,10-trimethyl-1-undecyl-magnesium chloride, prepared by the method of Example 1a from 0.92 g (38.5 millimoles) of magnesium and 8.72 g of (2R,6R)-1-chloro-2,6,10-trimethylundecane in 20 ml of THF, followed by 1.9 ml of an 0.5-molar solution of di-lithium tetrachlorocuprate in THF, were added to the above mixture at −20° C., and the batch was stirred for 3 hours at −20° C. and 15 hours at room temperature.

After having worked up the mixture by the method of Example 1c, bulb tube distillation at 230° C./0.2 mbar gave 8.1 g of (2R,4'R,8'R)-α-tocopherol. This corresponds to a yield of 75% of theory.

After conversion to the acetate in a conventional manner, the product exhibits an optical rotation of $[\alpha]^{25} = +3.0°$ (C=5.0 in ethanol)

EXAMPLE 7

6.26 g (20 millimoles) of (2RS)-2,5,7,8-tetramethyl-6-hydroxy-2-(2-bromoethyl)-chroman were dissolved in 20 ml of absolute THF. 16.2 ml of a 1.5-molar solution of vinyl-magnesium chloride in THF were added to the above solution at −20° C. and the mixture was stirred for 1 hour at the same temperature. Thereafter, a solution of (2RS,6RS)-1-chloro-2,6,10-trimethylundecyl-magnesium chloride, which had been prepared by reacting a solution of 0.86 g (35.8 millimoles) of magnesium in 10 ml of absolute THF with a solution of 8.16 g (34 millimoles) of (2RS,6RS)-1-chloro-2,6,10-trimethyl-undecane in 10 ml of THF and stirring the mixture for 2 hours at +70° C. was added dropwise to the above solution at −20° C., followed by dropwise addition of 1.4 ml of an 0.5-molar solution of di-lithium tetrachlorocuprate in absolute THF. The reaction mixture was then stirred for 3 hours at −20° C. and 15 hours at room temperature. After it had been worked up by the method of Example 1c, 3.3 g of α-tocopherol were isolated by distillation at 210° C./0.2 mbar. This corresponds to a yield of 38% of theory.

We claim:

1. A process for the preparation of α-tocopherol of the formula I

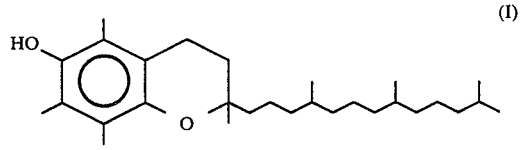
(I)

by reacting a chroman derivative with a C14-Grignard reagent using a di-alkali metal tetrahalocuprate catalyst in a Schlosser-Fouquet reaction, wherein (a) a chroman derivative of the formula II

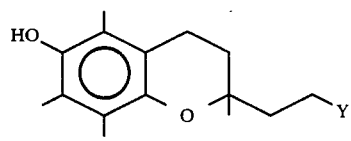
(II)

where Y is one of the leaving groups —Br, —I, -p-tosyl or benzenesulfonyl, especially —Br, is used and is reacted, at from −70° to 0° C., (b) first with a solution of from 0.8 to 1.1 equivalent of a Grignard reagent of the formula III X—Mg—R  (III)

where X is Cl, Br or I and R is straight-chain or branched alkyl of 1 to 14 carbon atoms, preferably methyl, ethyl or

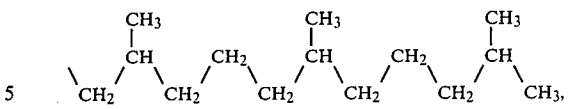

and then (c) with a solution of from 1.05 to 2 equivalents of a Grignard reagent of the formula IIIa

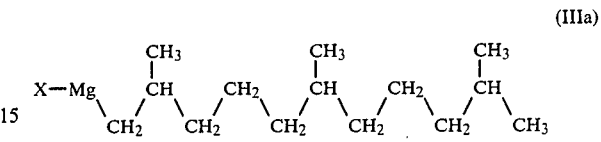
(IIIa)

in an ether solvent and in the presence of a solution of a di-alkali metal tetrahalocuprate in an ether solvent.

2. A process for the preparation of α-tocopherol of the formula I as claimed in claim 1, wherein the reaction of the chroman derivative of formula II with the solution of the Grignard reagent of the formula III and the Grignard reagent of the formula IIIa is carried out at from −25° to −15° C.

3. A process for the preparation of α-tocopherol of the formula I as claimed in claim 1, wherein the reaction with the solution of the Grignard reagent of the formula IIIa is carried out in the presence of a solution of di-lithium tetrachlorocuprate.

4. A process as claimed in claim 1, wherein, to prepare (2R,4'RS,8'RS)-α-tocopherol, an ether solution of (2S)-2,5,7,8-tetramethyl-6-hydroxy-2-(2'-bromoethyl)-chroman is reacted, in step (c), with a solution of a (2RS,6RS)-2,6,10-trimethyl-1-undecyl-magnesium halide.

5. A process as claimed in claim 1, wherein, to prepare (2R,4'R,8'R)-α-tocopherol, an ether solution of (2S)-2,5,7,8-tetramethyl-6-hydroxy-2-(2'-bromoethyl)-chroman is reacted, in step (c), with a solution of a (2R,6R)-2,6,10-trimethyl-1-undecyl-magnesium halide.

6. The process of claim 1, wherein the ether solvent comprises tetrahydrofuran, dioxane, diethylether, dimethoxyethane, diethylene glycol dimethyl ether or a mixture thereof.

7. The process of claim 1, wherein the ether solvent comprises tetrahydrofuran.

8. The process of claim 1, wherein R is methyl or ethyl, and X is Br.

9. The process of claim 1, wherein the two reactants of step (b) are reacted for from 15 minutes to 4 hours.

10. The process of claim 9, wherein the two reactants of step (b) are reacted for from 30 minutes to 2 hours.

11. The process of claim 1 wherein Y is Br.

12. The process of claim 1, wherein after the addition of the di-alkali metal tetrahalocuprate, the reaction mixture is stirred for from 2 to 3 hours at a temperture of from −70° to 0° C.

13. The process of claim 1 wherein the di-alkali metal tetrahalocuprate is used in an amount of about 0.5 to 4 mole % based on the Grignard compound IIIa employed.

* * * * *